United States Patent [19]
Hawke et al.

[11] 4,198,989
[45] Apr. 22, 1980

[54] TRANSDUCER HOLDER

[75] Inventors: David Hawke, LaVerne; M. Janet Kirkwood, Montebello, both of Calif.

[73] Assignee: Eaton Corporation, Cleveland, Ohio

[21] Appl. No.: 852,227

[22] Filed: Nov. 17, 1977

[51] Int. Cl.² .......................... A61B 5/02; A44C 5/00
[52] U.S. Cl. ..................................... 128/675; 128/133; 128/DIG. 6; 128/DIG. 26; 248/231; 224/222
[58] Field of Search ............... 128/2.05 D, 2.05 E, 128/214 E, DIG. 15, 214 R, DIG. 6, 215, DIG. 13, DIG. 26, 132, 133, 253, 327, 346; 224/5 R, 5 H, 5 F, 5 A, 5 B, 5 D, 26 R, 26 B, 28 R, 28 A, 28 B, 28 C, 28 D, 28 E, 28 G, 28 H, 28 F, 28 W, 267, 176, 270, 191, 219, 221, 222, 250; 248/444, 231, 74 PB, 118.5, 225; 108/43; 24/3 A, 81 CC, 16 R, 16 PB; 362/103, 105, 382

[56] References Cited

U.S. PATENT DOCUMENTS

| | | | |
|---|---|---|---|
| 2,024,281 | 12/1935 | Gaskin | 224/28 C |
| 3,059,645 | 10/1962 | Hasbrouck | 128/133 |
| 3,069,538 | 7/1962 | Hobson | 248/74 PB |
| 3,471,109 | 10/1969 | Meyer | 24/16 PB |
| 3,610,228 | 10/1971 | Temkin | 128/2.05 D |
| 3,812,851 | 5/1974 | Rodriguez | 128/133 |
| 4,002,337 | 1/1977 | Rayfield | 248/74 PB |

FOREIGN PATENT DOCUMENTS

| | | | |
|---|---|---|---|
| 371805 | 6/1923 | Fed. Rep. of Germany | 362/103 |
| 140275 | 8/1930 | Switzerland | 224/28 |
| 830397 | 3/1960 | United Kingdom | 362/105 |

Primary Examiner—Robert W. Michell
Assistant Examiner—Arthur S. Rose
Attorney, Agent, or Firm—Kevin Redmond

[57] ABSTRACT

A flexible pad with two self-securing straps for mounting a transducer to the arm of a patient.

4 Claims, 6 Drawing Figures

TRANSDUCER HOLDER

BACKGROUND

1. Field

This invention relates to improvements in the method of securing medical transducers to a patient's arm.

2. Prior Art

In the treatment of a patient, it is often important to monitor the patient's condition by means of a transducer. Typically the transducer is connected to the patient by way of a catheter and needle. For a transducer to operate properly, it generally must be maintained at some level, such as at the level of the patient's heart. The lower arm is often a suitable location for a transducer because the patient is normally careful to keep his lower arm at his side when a needle is inserted in the upper arm. This maintains the lower arm at the correct level with respect to the heart and the catheter length is short, extending only from the upper arm to the lower arm. Short catheter lengths are desired to facilitate patient care because they are easily kept out of the way.

There are two principal prior art methods of mounting a transducer. In the first, the transducer is simply secured to the patient's arm with gauze. In the second the transducer is supported at the desired level on a pole, some distance from the bed.

There are a number of problems with both of these methods. In the first, the transducer tends to twist as the patient moves. This in turn can cause the needle to twist in the patient's arm and can often result in severe pain.

In the second, a catheter 6 to 8 feet long is required to connect the transducer to the patient. The catheter is often curled across the top of the patient, encumbering nurses in caring for the patient. In addition, the transducer position must be changed each time the bed is raised or lowered to maintain it at the proper level and the probability of air entrapment is relatively high with the long catheter.

In either of these two methods, the setup time is long, the chance of obtaining an erroneous reading is relatively high, and the resulting arrngement is, at best, awkward.

SUMMARY

In accordance with the present invention, a flexible pad having two self-securing straps is quickly and easily applied to firmly hold a transducer to the patient's arm and thus avoid twisting the transducer as the patient moves. The pad and transducer may be quickly removed by simply cutting the straps. This device is sufficiently low in cost to discard it after use and provide a new sanitary device for each new application.

DETAILED DESCRIPTION OF THE INVENTION

Figure 1:
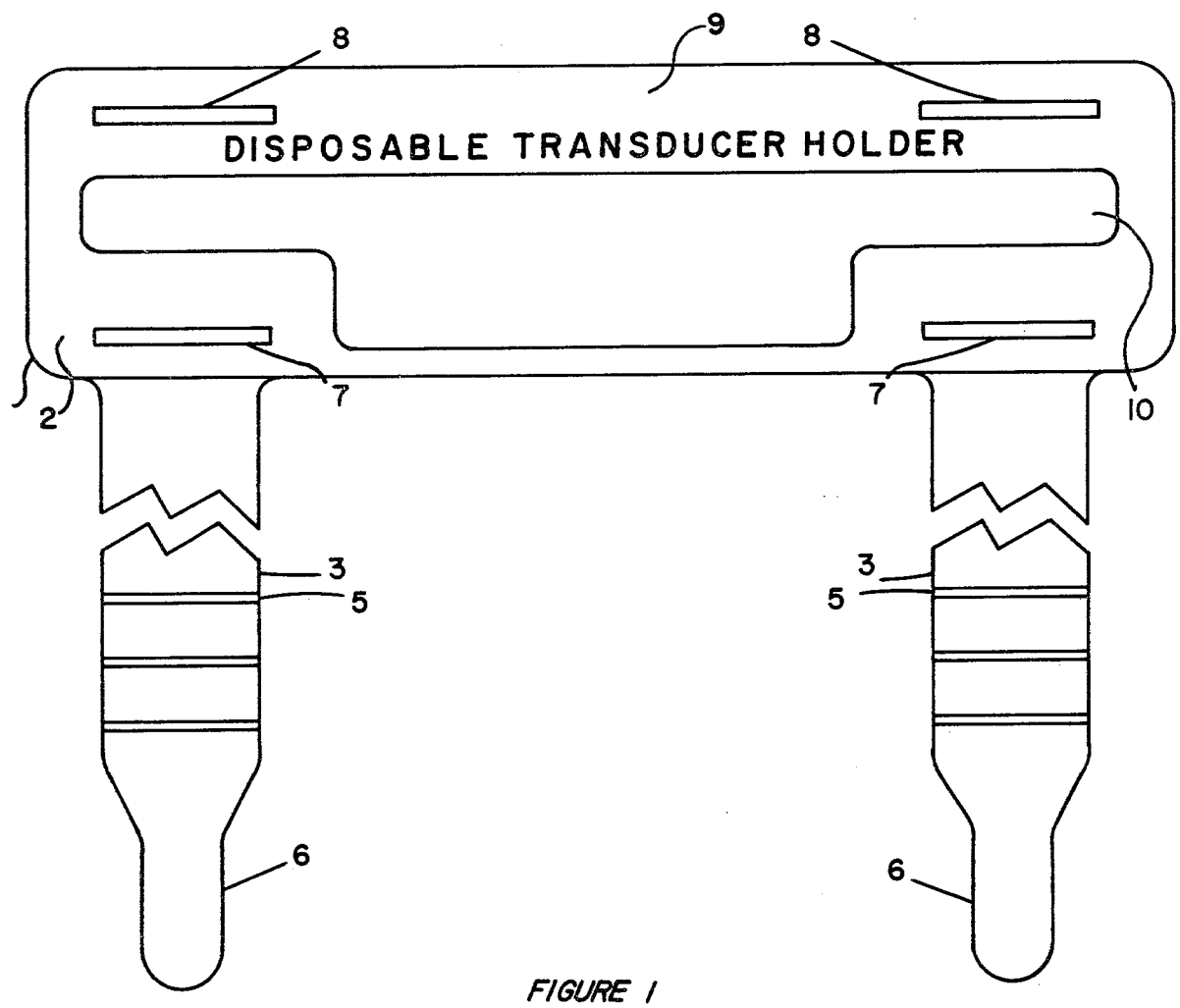
FIG. 1 is a plan view of a transducer holder.

Referring to FIG. 1, the holder 1 comprises a flexible pad 2 and two flexible self-securing straps 3. The pad 2 comprises an identification area 9, a depressed transducer area 10, two lower strap slots 7 and two upper strap slots 8. The straps 3 include tongues 6 and securing threads 5. The tongues 6 are narrower sections of the straps with a tongue-like appearance and rounded tips, located at the ends of the strap. The narrow tongues facilitate passing the straps through the strap slots.

Figure 2:
FIG. 2 is a side view of a transducer holder.

Referring to FIG. 2, it can be seen that the depressed transducer area 10 lies below the identification area 9. The upper slots 8 are generally perpendicular to the identification area while the lower slots are at an angle of nominally 45° with respect to the identification area. The threads 5 are seen in this view as raised portion of the upper surface of the straps 3.

Figure 3:
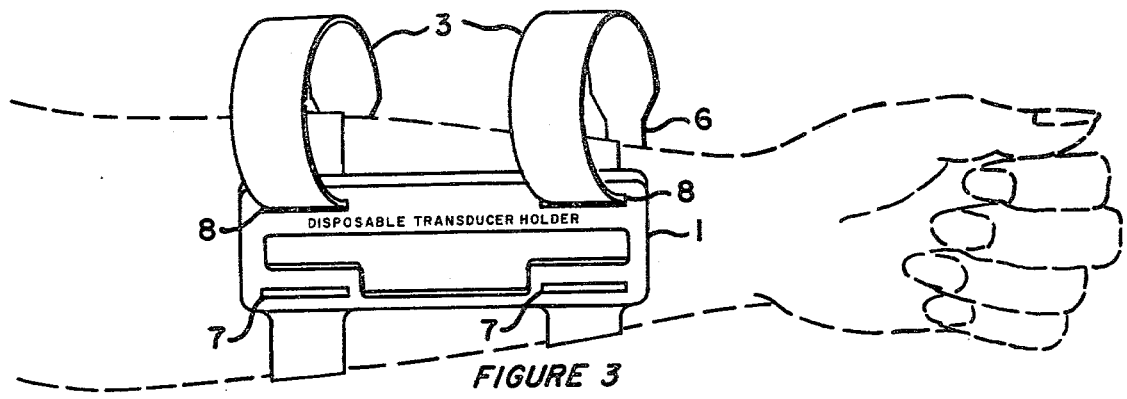
FIG. 3 illustrates a transducer holder secured to the forearm.

In FIG. 3, the first step in securing the holder to the lower arm is shown to be passing the straps around the arm and through the lower slots 7.

Figure 4:
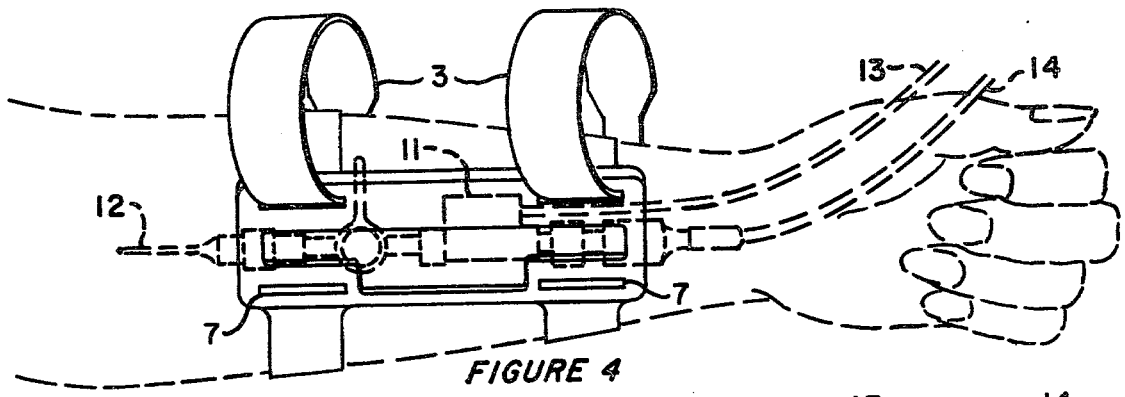
FIG. 4 illustrates the location of a transducer on the holder.

In FIG. 4, the next step is shown to be placing the transducer 11 in the depress transducer area of the pad while the catheter 12 and other lines such as lines 13 and 14 are dressed away from the holder.

Figure 5:
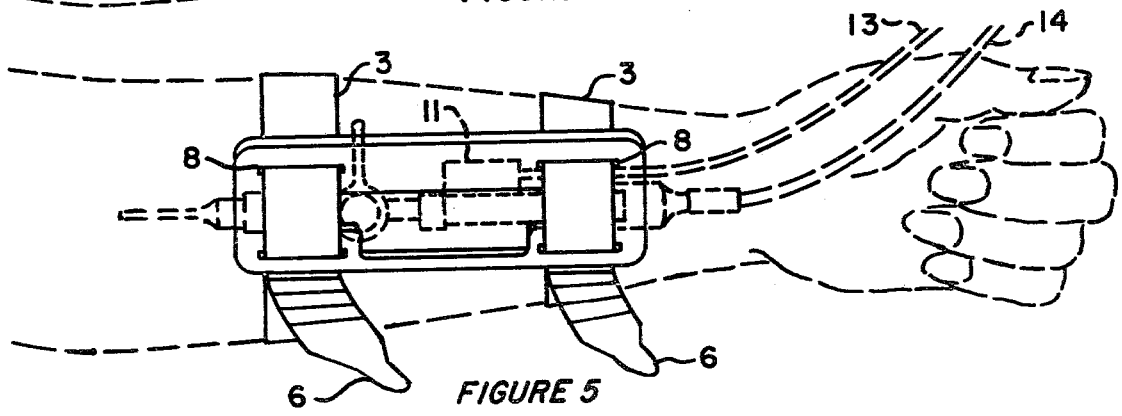
FIG. 5 illustrates the method by which the transducer is secured to the holder.

In FIG. 5, the transducer is shown secured to the holder by passing the straps through the upper slots 8. The tongue aids in passing the straps through the slots while the raised threads 5 prevent the straps from pulling back through the slots once installed. The slots provide a relatively tight fit for the straps while the tension on the straps causes the threads to catch against the outside edge of the slots and thus prevent the straps from unfastening once they have been secured.

Figure 6:
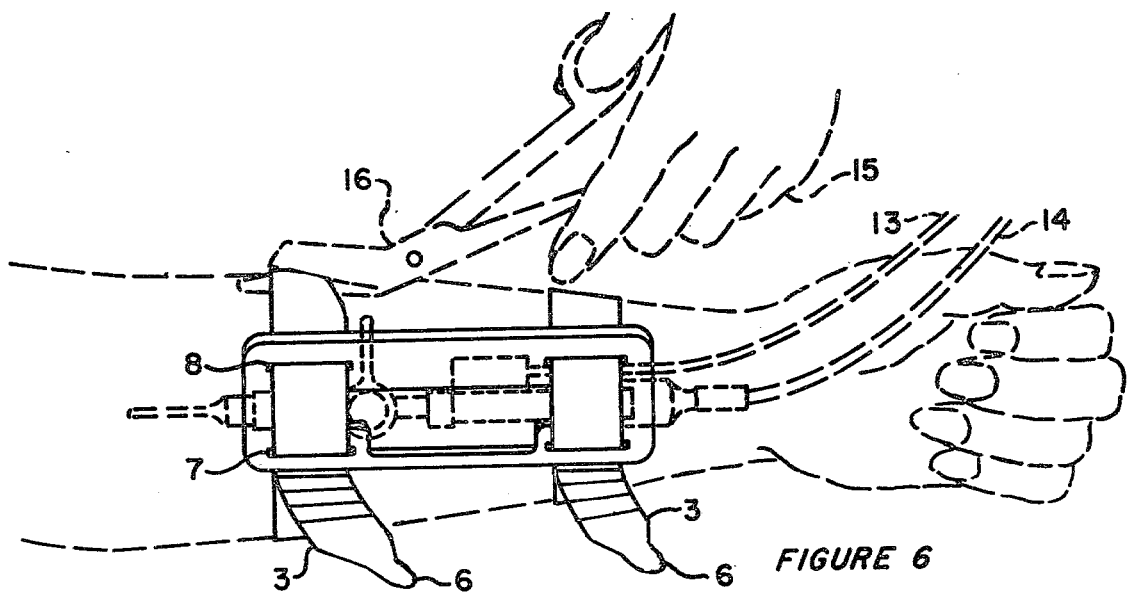
FIG. 6 illustrates the method of removing the holder.

FIG. 6 shows that the transducer may easily be removed by shearing the straps.

Having described our invention, we claim:

1. A single piece transducer holder to secure a transducer to a limb, comprising:
    (a) a generally flat, rectangularly shaped, flexible and smooth surfaced pad having an elongated depressed central area, said area having a width that varies along its length corresponding to the general outline of said transducer to hold a transducer in place on the pad and said pad including four rectangularly shaped strap slots located adjacent the corners of said pad with the slot openings aligned generally parallel to each other and generally parallel to one side of the pad,
    (b) two elongated straps with a cross section generally corresponding to said rectangularly shaped strap slots, said straps being of a length sufficient to surround simultaneously both the limb of a person and the width of a transducer, said straps being attached at one end to a side of said pad that is aligned parallel to said slots to form a single piece holder, said straps being threadable through said slots, and (c) means for holding said straps in a desired position with respect to said slots.

2. A transducer holder as claimed in claim 1, wherein said means for holding comprises:
    (a) a plurality of threads formed of raised portions of the upper face of the straps, arranged generally perpendicularly to the longitudinal axis of the straps to hold the straps securely in place against the outside portion of said slots once they have been passed through said slots, and (b) said straps further comprising tongue shaped ends to facilitate feeding the strap through said slots.

3. A method for securing a transducer to a patient's limb comprising the steps of:
  (a) providing a generally rectangularly shaped pad having a depressed elongated area, said area having a width that varies along its length to accept and hold the transducer, four generally rectangularly shaped slots located adjacent the corners of said pad and aligned generally parallel to each other and parallel to one side of said pad,
  (b) providing two straps attached to a side of said pad that is aligned with said slots, said straps being threadable through said slots,
  (c) providing means for holding said straps in a desired position with respect to said slots,
  (d) passing the straps about the limb,
  (e) passing the straps through the set of slots on the side away from the side of attachment of the straps to the pad,
  (f) placing the transducer on the pad in the depressed area,
  (g) passing the straps over the transducer, and
  (h) passing the straps through the remaining set of slots.

4. A method as claimed in claim 3, wherein the step of providing holding means comprises,
  providing a plurality of threads on the upper surface of the straps formed of raised portions of the strap on the upper surface of the straps, said threads being aligned generally perpendicularly to the longitudinal axis of the strap to hold the straps in place once passed through the slots, and
  said method further comprises providing tongue shaped ends for the straps to facilitate passing said straps through said slots.

* * * * *